United States Patent
Sowwan et al.

(10) Patent No.: US 12,415,982 B2
(45) Date of Patent: Sep. 16, 2025

(54) AUTOMATED CLOSED SYSTEM FOR CELL THERAPY MANUFACTURING

(71) Applicant: APPLIED MATERIALS, INC., Santa Clara, CA (US)

(72) Inventors: Mukhles Sowwan, Cupertino, CA (US); Samer Banna, San Jose, CA (US)

(73) Assignee: APPLIED MATERIALS, INC., Santa Clara, CA (US)

( * ) Notice: Subject to any disclaimer, the term of this patent is extended or adjusted under 35 U.S.C. 154(b) by 281 days.

(21) Appl. No.: 17/505,627

(22) Filed: Oct. 20, 2021

(65) Prior Publication Data

US 2022/0127558 A1 Apr. 28, 2022

Related U.S. Application Data

(60) Provisional application No. 63/105,192, filed on Oct. 23, 2020.

(51) Int. Cl.
*C12M 1/36* (2006.01)
*C12M 1/00* (2006.01)
*C12M 1/26* (2006.01)

(52) U.S. Cl.
CPC ............ *C12M 41/48* (2013.01); *C12M 33/00* (2013.01); *C12M 39/00* (2013.01)

(58) Field of Classification Search
CPC ...... C12M 41/48; C12M 33/00; C12M 39/00; C12M 23/58; C12M 37/00
See application file for complete search history.

(56) References Cited

U.S. PATENT DOCUMENTS 11,230,690 B2 * 1/2022 Cannon .................. C12M 41/14
2004/0081457 A1 4/2004 Britcher et al.
2017/0037369 A1 2/2017 Ramsborg et al.
2019/0169572 A1 6/2019 Shi et al.
2020/0141942 A1 5/2020 Miltenyi et al.

FOREIGN PATENT DOCUMENTS

WO WO-2009072003 A2 * 6/2009 ......... A61K 39/4611
WO WO 2020/152509 A1 7/2020

OTHER PUBLICATIONS

Wu, Y. et al., 'Automated closed systems for cell manufacturing', Cytotherapy, 2019, vol. 21, No. 5, p. S41.
Moutsatsou, P. et al., 'Automation in cell and gene therapy manufacturing: from past to future', Biotechnology letters, 2019, vol. 41, pp. 1245-1253.
PCT International Search Report and Written Opinion for PCT/US2021/056380 dated Feb. 16, 2022.

* cited by examiner

*Primary Examiner* — Fereydoun G Sajjadi
*Assistant Examiner* — Masudur Rahman
(74) *Attorney, Agent, or Firm* — Moser Taboada

(57) ABSTRACT

Embodiments of automated closed apparatus for cell therapy manufacturing are provided herein. In some embodiments, an automated closed apparatus for cell therapy manufacturing includes: a master device having a master controller for processing control programs for a variety of cell types; an input device fluidly coupled to the master device, wherein the input device is configured to feed an initial plurality of cells to the master device; one or more auxiliary devices each configured to perform one or more cell therapy manufacturing steps to the initial plurality of cells to form a final plurality of cells; and an output device coupled to the master device configured to collect the final plurality of cells from the master device.

20 Claims, 4 Drawing Sheets

# AUTOMATED CLOSED SYSTEM FOR CELL THERAPY MANUFACTURING

CROSS-REFERENCE TO RELATED APPLICATIONS

This application claims benefit of U.S. provisional patent application Ser. No. 63/105,192, filed Oct. 23, 2020, which is herein incorporated by reference in its entirety.

FIELD

Embodiments of the present disclosure generally relate to cell therapy equipment.

BACKGROUND

Cell therapy is a therapy in which viable cells are infused or transplanted into the patient to achieve a therapeutic effect against cancer, disease or genetic disorder. For example, CAR-T cell therapy is a form of immunotherapy that uses gene modified T cells, a type of white blood cells, to fight cancer. The current conventional process of manufacturing these modified cells involves several steps that include enrichment of peripheral blood mononuclear cells (PBMCs) from whole blood, umbilical cord blood, or leukapheresis, wash to get rid of debris and contamination and concentrate the T cells in suitable container for the next step in the process, T cell selection for further gene modification, T cell activation and genetic modification (transduction or transfection), a bioreactor for T cell expansion to reach the required yield or therapeutic dose, and harvest, finish, and formulate the modified cells into a final therapeutic product.

However, the use of multiple and separate devices in the manufacturing process requires significant labor allocation, support, and expensive infrastructure. Even with systems that may support multiple processes in a single device, the systems are predefined and therefore not modularized (produced into modules to be integrated into a platform utilizing a well-defined modular interface). Subsequent exchange of a device in use within the system cannot be carried out due the high cost associated with changing the system configuration.

Accordingly, the inventors have provided an improved automated reconfigurable and modular closed system for cell therapy manufacturing.

SUMMARY

Embodiments of automated closed apparatus and methods for cell therapy manufacturing are provided herein. In some embodiments, an automated closed apparatus for cell therapy manufacturing includes: a master device having a master controller for processing control programs for a variety of cell types; an input device fluidly coupled to the master device, wherein the input device is configured to feed an initial plurality of cells to the master device; one or more auxiliary devices each configured to perform one or more cell therapy manufacturing steps to the initial plurality of cells to form a final plurality of cells, wherein each of the one or more auxiliary devices is removably coupled to the master device, wherein, when coupled to the master device, each device of the one or more auxiliary devices is (1) fluidly coupled to the master device via one or more transfer lines to facilitate transfer of at least a portion of the initial plurality of cells therebetween; and (2) electrically coupled to the master device to facilitate transfer of data therebetween, wherein the master device facilitates the plurality of cell therapy manufacturing steps via the one or more auxiliary devices; and an output device coupled to the master device configured to collect the final plurality of cells from the master device.

In some embodiments, a method for processing a plurality of cells in an automated closed apparatus includes feeding a plurality of initial cells to a master device of an automated closed apparatus via an input device; transferring at least a subset of the plurality of initial cells from the master device to and from one or more auxiliary devices via an input line and an output line of each auxiliary device for processing at least the subset of the plurality of initial cells to form a plurality of final cells, wherein the one or more auxiliary devices are removably coupled to the master device, and wherein the master device is configured to provide instructions to the one or more auxiliary devices for a variety of cell types; and transferring the plurality of final cells to an output device coupled to the master device to collect the plurality of final cells.

In some embodiments, a non-transitory computer readable medium for storing computer instructions that, when executed by at least one processor causes the at least one processor to perform a method includes: feeding a plurality of initial cells to a master device of an automated closed apparatus via an input device; transferring at least a subset of the plurality of initial cells from the master device to and from one or more auxiliary devices via an input line and an output line of each auxiliary device for processing at least the subset of the plurality of initial cells to form a plurality of final cells, wherein the one or more auxiliary devices are removably coupled to the master device, and wherein the master device is configured to provide instructions to the one or more auxiliary devices for a variety of cell types; and transferring the plurality of final cells to an output device coupled to the master device to collect the plurality of final cells.

Other and further embodiments of the present disclosure are described below.

BRIEF DESCRIPTION OF THE DRAWINGS

Embodiments of the present disclosure, briefly summarized above and discussed in greater detail below, can be understood by reference to the illustrative embodiments of the disclosure depicted in the appended drawings. However, the appended drawings illustrate only typical embodiments of the disclosure and are therefore not to be considered limiting of scope, for the disclosure may admit to other equally effective embodiments.

To facilitate understanding, identical reference numerals have been used, where possible, to designate identical elements that are common to the figures. The figures are not drawn to scale and may be simplified for clarity. Elements and features of one embodiment may be beneficially incorporated in other embodiments without further recitation.

DETAILED DESCRIPTION

Embodiments of an automated closed apparatus for cell therapy manufacturing and methods for processing a plurality of cells in an automated closed apparatus are provided herein. Automation and closing the manufacturing process for cell therapy manufacturing can significantly reduce the cost, increase the efficiency, and improve safety. A closed process is a process where the cells are never exposed to the open environment even between the different manufacturing steps. Applying a closed process advantageously reduces the risk of contamination and enables increased control and automation, which in turn can reduce timeline and cost.

The automated closed apparatus provided herein may advantageously be modularized to allow an end user to configure parts of the automated closed apparatus. For example, to isolate a cell type from a heterogeneous population of cells depends on the unique properties of that cell type, such as density, size or morphology. For density-based separation, a centrifuging device is used, for size-based separation, a microfluidic based device is used, while for morphology-based separation, a high-resolution optical microscope is used. Thus, the automated closed apparatus provided herein allows to subsequently connect a new device (to exchange one technology with another or an old device with a new device), creating a modular system.

The apparatus and methods provided herein provide a universal system for cell therapy manufacturing with the capability to manufacture various cell therapy types in a modular but closed and fully automated manner. The system has a master device having a master controller to control, transmit and collect data. The master device may be coupled to an input device configured to feed an initial plurality of cells to the master device. The initial plurality of cells may contain cells such as T cells, stem cells, or the like. The master device may be coupled to an output device configured to collect a final plurality of cells from the master device. The master controller can communicate with the input device, the output device, and one or more auxiliary devices (the input device, the output device, and the one or more auxiliary devices collectively known as devices of the system). The master controller includes control programs for actuating, for example, via device interfaces, the devices of the system.

According to the present disclosure, reconfigurable hardware is used in all interfaces and devices, thus advantageously facilitating adding new devices to the platform or replacing an old device with a new device based on the same or different technology in the future and/or based on changing needs.

Figure 1:
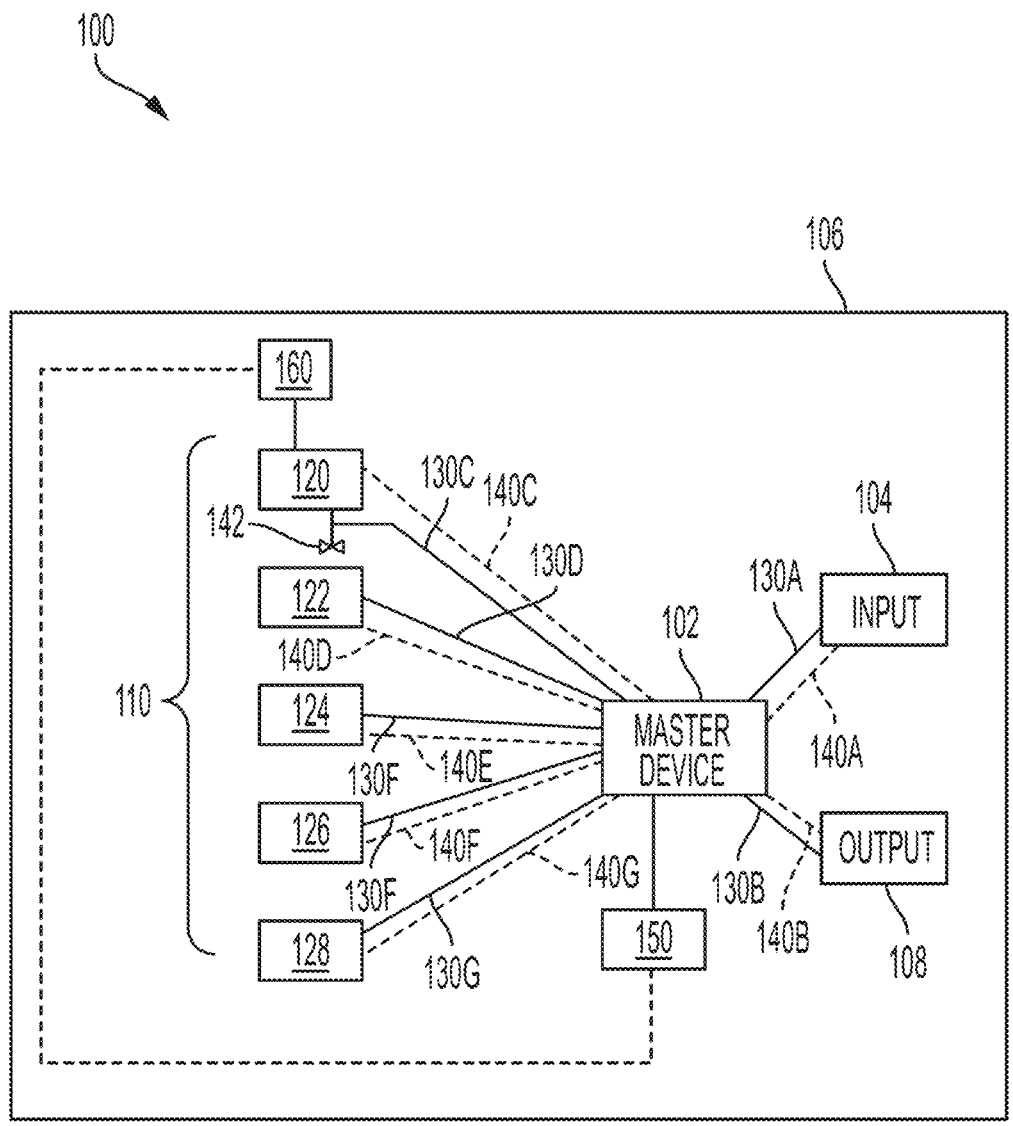
FIG. 1 depicts a schematic view of an automated closed apparatus for cell therapy manufacturing in accordance with at least some embodiments of the present disclosure.

FIG. 1 depicts a schematic view of an automated closed apparatus for cell therapy manufacturing in accordance with at least some embodiments of the present disclosure. In some embodiments, the automated closed apparatus 100 is disposed in an enclosed housing 106 having a suitable shape. In some embodiments, the automated closed apparatus 100 is not disposed in an enclosed housing. The automated closed apparatus 100 is configured to receive an initial plurality of cells as a physical input, perform one or more processes on the initial plurality of cells, and provide a physical output in the form of a final plurality of cells. The automated closed apparatus 100 includes a master device 102 having a master controller 150 for controlling the automated closed apparatus 100. The master controller 150 generally processes control programs or processes artificial intelligence algorithms, such as machine learning algorithms, and is described in more detail below with respect to FIG. 2. The master controller 150 may also generally transmit instructions and collect data from the various devices described below.

An input device 104 is fluidly coupled to the master device 102 to feed an initial plurality of cells to be processed to the master device 102. In some embodiments, at least one of the input device 104 and the master device 102 may include a suitable cell counter or other cell monitoring tool to characterize at least one of a size, morphology, quantity, or type of the initial plurality of cells. An output device 108 is fluidly coupled to the master device 102 and configured to collect the final plurality of cells from the master device 102. The output device 108 may perform a finish and fill process to provide a final therapeutic product. In some embodiments, at least one of the output device 108 and the master device 102 may include a suitable cell counter or other cell monitoring tool to characterize at least one of a size, morphology, quantity, or type of the final plurality of cells. The input device 104 and the output device 108 may be connected to sensors, optical microscopes, or the like, to perform the desired cell monitoring function.

On or more fluid transfer lines may fluidly couple the master device 102 to other devices in the automated closed apparatus 100. For example, one or more of the input device 104 and the output device 108 are standalone devices that are fluidly coupled to the master device 102 via one or more fluid transfer lines 130A and 130B, respectively. In some embodiments, the input device 104 and the output device 108 are integrally formed with the master device 102 in the form of an input port and an output port. In some embodiments, the input device 104 is electrically coupled via conduit 140A to the master device 102 to facilitate transfer of data therebetween. In some embodiments, the output device 108 is electrically coupled via conduit 140B to the master device 102 to facilitate transfer of data therebetween.

The automated closed apparatus 100 includes one or more auxiliary devices each configured to perform one or more cell therapy manufacturing steps to the initial plurality of cells to form the final plurality of cells. Each of the one or more auxiliary devices 110 is removably coupled to the master device 102 so that the automated closed apparatus 100 is modularized. That is, the one or more auxiliary devices 110 are configured to be "plug and play" so that the automated closed apparatus 100 may be customized to perform one or more desired process(es) on a variety of cell types for use with a variety of cell therapies. In some embodiments, the one or more auxiliary devices 110 include at least one of the input device 104 and the output device 108.

Each device of the one or more auxiliary devices 110 may be fluidly coupled to the master device 102 via one or more transfer lines 130C-130G to facilitate transfer of at least a portion of the initial plurality of cells therebetween. In some embodiments, each of the one or more transfer lines 130C-130G may be a single line (where input line and outline line are the same line) to deliver fluid from the master device 102 to a respective one of the one or more auxiliary devices 110 and back to the master device 102. In some embodiments, each of the one or more transfer lines 130C-130G may be comprise an input line from the master device 102 to one of the one or more auxiliary devices 110 and an output line, separate from the input line, from one of the one or more auxiliary devices 110 back to the master device 102. In some embodiments, at least one of the one or more transfer lines 130C-130G include a control valve 142 to control a flow therethrough.

Each device of the one or more auxiliary devices 110 may be electrically coupled to the master device 102 via respective conduits 140C-140G to facilitate transfer of data therebetween. The master device 102 facilitates the plurality of cell therapy manufacturing steps via the one or more auxiliary devices 110. In some embodiments, at least one of the one or more auxiliary devices 110 include a controller 160 configured to communicate with the master controller 150 of the master device 102. In some embodiments, at least one of the one or more auxiliary devices 110 may be configured to perform a cell characterization process or other diagnostic or measurement process. The one or more auxiliary devices 110 may include one or more sensors provide data inputs for the master controller 150.

The one or more auxiliary devices 110 may perform any suitable processing step on at least a portion of the initial plurality of cells. In some embodiments, the one or more auxiliary devices 110 are configured to perform at least two of the following on at least a portion of the plurality of initial cells: a chemical enrichment process, a cleaning process to remove contamination, a cell selection process, an activation, transduction, or transfection process, a perfusion process, a cell expansion process to form the plurality of final cells, and a fill and finish process.

For example, the one or more auxiliary devices 110 may include a first device 120 configured to perform an analysis or diagnosis process or a chemical enrichment process on at least a portion of the plurality of initial cells. The chemical enrichment process may comprise supplying a medium to the at least portion of the plurality of initial cells to isolate desired cells (for example, T cells or stem cells) and target other unwanted cells for removal.

In some embodiments, the one or more auxiliary devices 110 may include a second device 122 configured to perform a cleaning process on at least a portion of the plurality of initial cells to remove contamination and unwanted cells. The cleaning process may generally be conducted via filtration or sedimentation. In some embodiments, the cleaning process is performed after the chemical enrichment process.

In some embodiments, the one or more auxiliary devices 110 may include a third device 124 configured to perform a cell selection process to select a subset, or type, of the plurality of initial cells for gene modification. The cell selection process may be performed based on size, density, morphology of the desired cells. The cell selection process may employ at least one of a centrifuging device, a microfluidic based device, a high-resolution optical device, a filtration device, or the like, depending on the type of cells desired. In some embodiments, the cell selection process is performed after the cleaning process.

In some embodiments, the one or more auxiliary devices 110 may include a fourth device 126 configured to perform an activation, transduction, transfection, or any other gene modification process on a subset of the plurality of initial cells. The subset of the plurality of initial cells may be the cells selected after the cell selection process. Activation generally comprises presenting the subset of the plurality of initial cells with a foreign substance, or antigens, that induces a response to the subset of the plurality of initial cells. Once activated, the subset of the plurality of initial cells may divide rapidly. Generally, transfection is the process of introducing nucleic acids into cells by non-viral methods and transduction is the process whereby foreign DNA is introduced into another cell via a viral vector. These are common tools to introduce a foreign gene into host cells (e.g., the subset of the plurality of initial cells), and thereby perform a gene modification process.

In some embodiments, the one or more auxiliary devices 110 may include a fifth device 128 configured to perform a cell expansion process for multiplying a subset of the plurality of initial cells to form the plurality of final cells. The subset of the plurality of initial cells may the resultant cells after an activation, transduction, or transfection process. The fifth device 128 may be a bioreactor for performing the cell expansion process.

Figure 4:
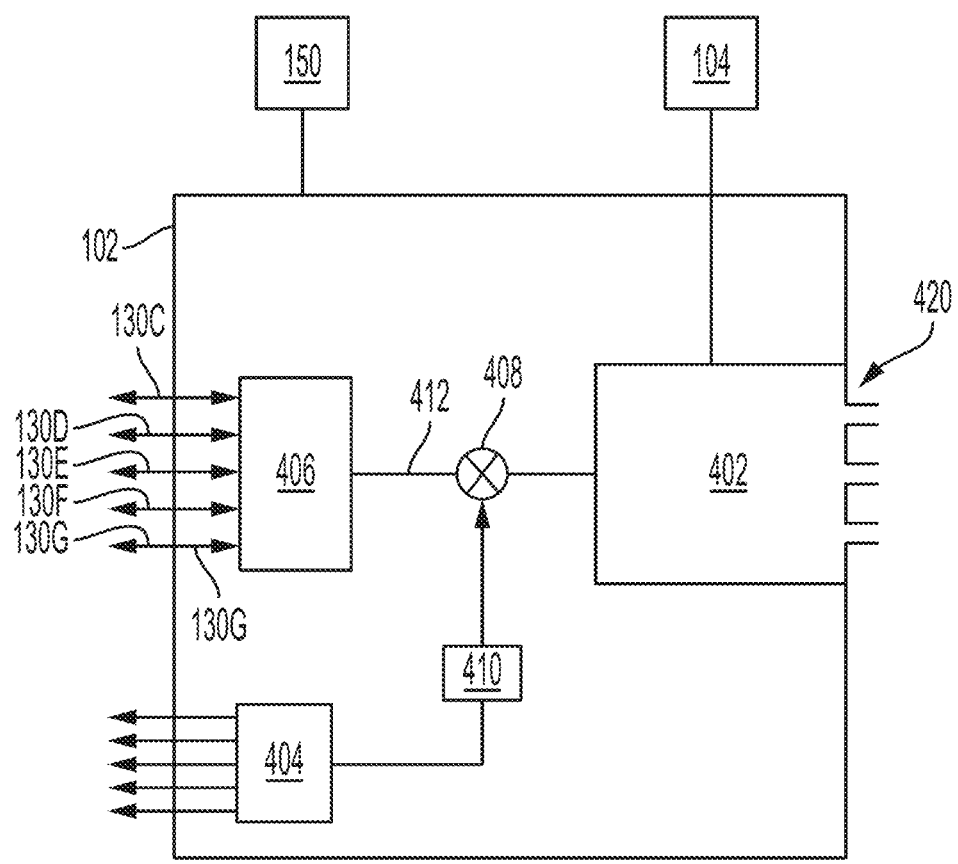
FIG. 4 depicts a schematic view of a master device in accordance with at least some embodiments of the present disclosure.

FIG. 4 depicts a schematic view of a master device 102 in accordance with at least some embodiments of the present disclosure. In some embodiments, the master device 102 includes a reservoir 402 fluidly coupled to the input device 104 via transfer line 412. The reservoir 402 is a container for storing a fluid containing the plurality of initial cells. In some embodiments, the reservoir 402 includes one or more ports 420 for in-line monitoring devices and sensors. In some embodiments, the one or more ports 420 may facilitate coupling the reservoir 402 to one or more sensors for monitoring one or more of O2 levels, pH, CO2 levels, temperature, or pressure. In some embodiments, the one or more ports 420 may be coupled to optical microscopes, cell counters, or the like.

In some embodiments, the reservoir 402 is fluidly coupled to a flow control switch 406. The flow control switch 406 is configured to direct fluids between the master device 102 and the one or more auxiliary devices 110. The flow control switch 406 generally includes re-routable fluid connections such that fluid from the one or more auxiliary devices 110 can be routed to any other one of the one or more auxiliary devices 110 via the flow control switch 406. The flow control switch 406 may be coupled to the master controller 150 to control circulation or sequential routing of fluid as needed based on the manufacturing process protocol (automated fluid routing from one step to another). The flow control switch 406 may includes a plurality of ports coupled to respective fluid delivery lines (e.g., one or more fluid transfer lines 130C-130G) extending to the one or more auxiliary devices 110. The plurality of ports may be configured to allow for quick and ease of reconfiguration of the one or more auxiliary devices 110. The flow control switch 406 may comprise a plurality of multi-directional valves.

In some embodiments, a flow valve 408 may be disposed between the reservoir 402 and the flow control switch 406 to regulate fluid flow therebetween. In some embodiments, a pressure system 410 is fluidly coupled to the flow valve 408 to control a pressure of the transfer line 412. The pressure system 410 may comprise a pump. In some embodiments, the pressure system 410 may comprise a pump coupled to a throttle valve for regulating pressure. In some embodiments, a pressure manifold 404 is fluidly coupled to the pressure system 410. The pressure manifold 404 is configured to direct a pressurized flow into one or more of the one or more auxiliary devices 110. For example, the pressure manifold 404 may direct pressurized flow when needed to perform a cell therapy process or for directing fluid flow through one or more of the one or more auxiliary devices 110 or back to the master device 102.

Figure 2:
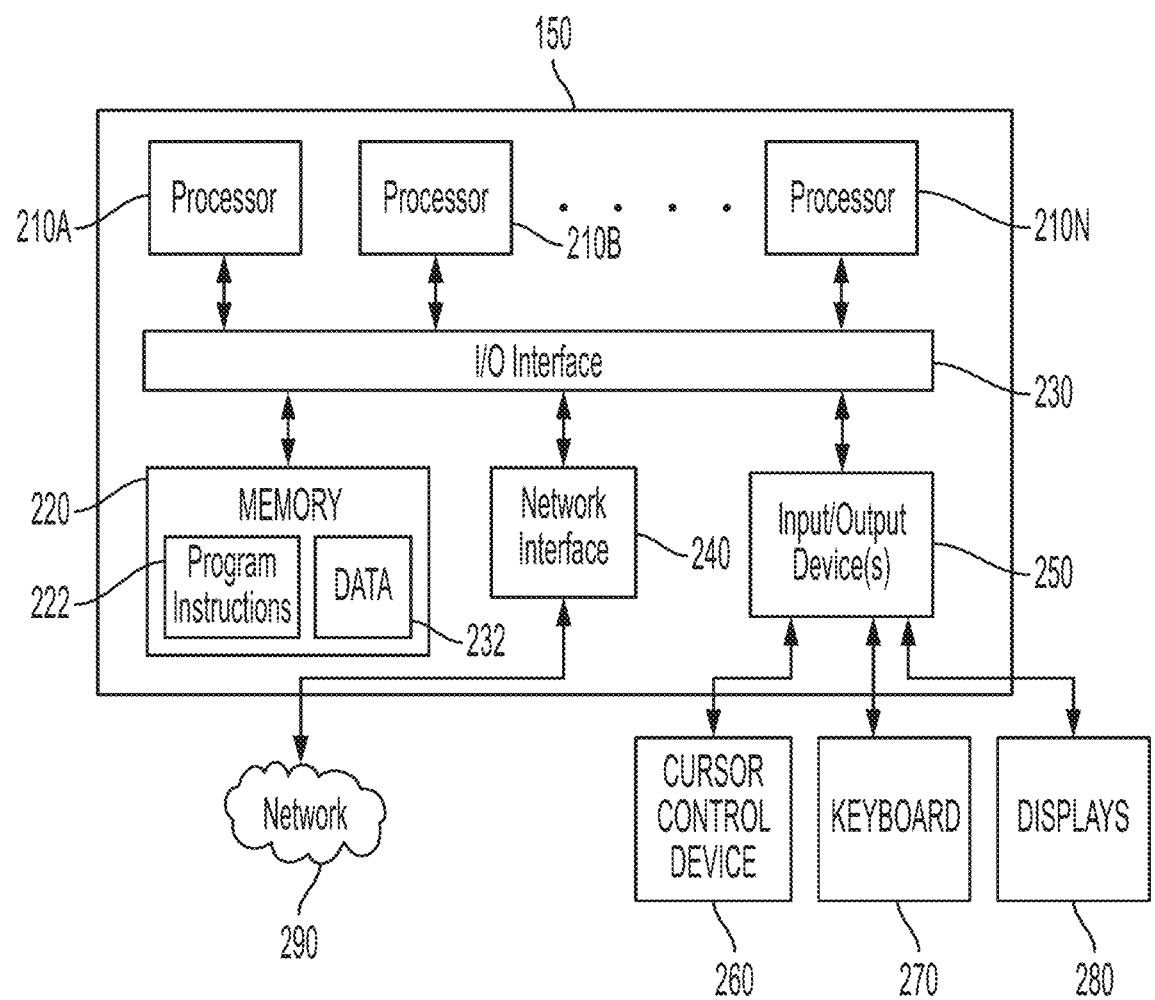
FIG. 2 depicts a high-level block diagram of a master controller of automated closed apparatus for cell therapy manufacturing in accordance with at least some embodiments of the present disclosure.

FIG. 2 depicts a high-level block diagram of a master controller 150 of an automated closed apparatus for cell therapy manufacturing in accordance with at least some embodiments of the present disclosure. Various embodiments of the automated closed apparatus for cell therapy manufacturing, as described herein, may be executed using one or more controllers, which may interact with each other, and which may interact with various other devices. One such controller is the master controller 150. In some embodiments, the master controller 150 may be configured to implement methods described herein. The master controller 150 may be used to implement any other system, device, element, functionality, or method of the herein-described embodiments. In some embodiments, the master controller 150 may be configured to implement the method 300 of FIG. 3 as processor-executable program instructions 222 (e.g., program instructions executable by processor(s) 210) in various embodiments. In some embodiments, one or more of the one or more auxiliary devices 110 may include a respective controller to interact with the master controller 150.

In some embodiments, the master controller 150 includes one or more processors 210A-210N coupled to a system memory 220 via an input/output (I/O) interface 230. Master controller 150 may further include a network interface 240 coupled to the I/O interface 230, and one or more input/output devices 250, such as cursor control device 260, keyboard 270, and display(s) 280. In various embodiments, any of the components may be utilized by the system to receive user input described above. In various embodiments, a user interface may be generated and displayed on display 280. In some cases, embodiments may be implemented using a single instance of master controller 150, while in other embodiments multiple such systems, or multiple nodes making up the master controller 150, may be configured to host different portions or instances of various embodiments. For example, in one embodiment some elements may be implemented via one or more nodes of master controller 150 that are distinct from those nodes implementing other elements. In another example, multiple nodes may implement master controller 150 in a distributed manner.

In some embodiments, the master controller 150 may be any of various types of devices, including, but not limited to, a personal computer system, desktop computer, laptop, notebook, tablet or netbook computer, mainframe computer system, handheld computer, workstation, network computer, or in general any type of computing or electronic device.

In various embodiments, the master controller 150 may be a uniprocessor system including one processor 210, or a multiprocessor system including several processors 210 (e.g., two, four, eight, or another suitable number). Processors 210 may be any suitable processor capable of executing instructions. For example, in various embodiments, processors 210 may be general-purpose or embedded processors implementing any of a variety of instruction set architectures (ISAs). In multiprocessor systems, each of processors 210 may commonly, but not necessarily, implement the same ISA.

System memory 220 may be configured to store program instructions 222 and/or data 232 accessible by processor 210. In various embodiments, system memory 220 may be implemented using any suitable memory technology, such as static random-access memory (SRAM), synchronous dynamic RAM (SDRAM), nonvolatile/Flash-type memory, or any other type of memory. In the illustrated embodiment, program instructions and data implementing any of the elements of the embodiments described above may be stored within system memory 220. In other embodiments, program instructions and/or data may be received, sent or stored upon different types of computer-accessible media or on similar media separate from system memory 220 or the master controller 150.

In one embodiment, I/O interface 230 may be configured to coordinate I/O traffic between processor 210, system memory 220, and any peripheral devices in the device, including network interface 240 or other peripheral interfaces, such as input/output devices 250. In some embodiments, I/O interface 230 may perform any necessary protocol, timing or other data transformations to convert data signals from one component (e.g., system memory 220) into a format suitable for use by another component (e.g., processor 210). In some embodiments, I/O interface 230 may include support for devices attached through various types of peripheral buses, such as a variant of the Peripheral Component Interconnect (PCI) bus standard or the Universal Serial Bus (USB) standard, for example. In some embodiments, the function of I/O interface 230 may be split into two or more separate components, such as a north bridge and a south bridge, for example. Also, in some embodiments some or all of the functionality of I/O interface 230, such as an interface to system memory 1620, may be incorporated directly into processor 210.

Network interface 240 may be configured to allow data to be exchanged between the master controller 150 and other devices attached to a network (e.g., network 290), such as one or more external systems or between nodes of master controller 150. In various embodiments, network 290 may include one or more networks including but not limited to Local Area Networks (LANs) (e.g., an Ethernet or corporate network), Wide Area Networks (WANs) (e.g., the Internet), wireless data networks, some other electronic data network, or some combination thereof. In various embodiments, network interface 240 may support communication via wired or wireless general data networks, such as any suitable type of Ethernet network, for example; via digital fiber communications networks; via storage area networks such as Fiber Channel SANs, or via any other suitable type of network and/or protocol.

Input/output devices 250 may, in some embodiments, include one or more display terminals, keyboards, keypads, touchpads, scanning devices, voice or optical recognition devices, or any other devices suitable for entering or accessing data by one or more computer systems 200. Multiple input/output devices 250 may be present in master controller 150 or may be distributed on various nodes of master controller 150. In some embodiments, similar input/output devices may be separate from master controller 150 and may interact with one or more nodes of master controller 150 through a wired or wireless connection, such as over network interface 240.

Those skilled in the art will appreciate that master controller 150 is merely illustrative and is not intended to limit the scope of embodiments. In particular, the computer system and devices may include any combination of hardware or software that can perform the indicated functions of various embodiments, including computers, network devices, Internet appliances, PDAs, wireless phones, pagers, and the like. Master controller 150 may also be connected to other devices that are not illustrated, or instead may operate as a stand-alone system. In addition, the functionality provided by the illustrated components may in some embodiments be combined in fewer components or distributed in additional components. Similarly, in some embodiments, the functionality of some of the illustrated components may not be provided and/or other additional functionality may be available.

Those skilled in the art will also appreciate that, while various items are illustrated as being stored in memory or on storage while being used, these items or portions of them may be transferred between memory and other storage devices for purposes of memory management and data integrity. Alternatively, in other embodiments some or all of the software components may execute in memory on another device and communicate with the illustrated computer system via inter-computer communication. Some or all of the system components or data structures may also be stored (e.g., as instructions or structured data) on a computer readable medium that is non-transitory or a portable article to be read by an appropriate drive, various examples of which are described above. In some embodiments, instructions stored on a computer readable medium separate from master controller 150 may be transmitted to master controller 150 via transmission media or signals such as electrical, electromagnetic, or digital signals, conveyed via a communication medium such as a network and/or a wireless link. Various embodiments may further include receiving, sending or storing instructions and/or data implemented in accordance with the foregoing description upon a computer readable medium or via a communication medium. In general, a computer readable medium may include a storage medium or memory medium such as magnetic or optical media, e.g., disk or DVD/CD-ROM, volatile or non-volatile media such as RAM (e.g., SDRAM, DDR, RDRAM, SRAM, and the like), ROM, and the like.

The methods described herein may be implemented in software, hardware, or a combination thereof, in different embodiments. In addition, the order of methods may be changed, and various elements may be added, reordered, combined, omitted or otherwise modified. All examples described herein are presented in a non-limiting manner. Various modifications and changes may be made as would be obvious to a person skilled in the art having benefit of the present disclosure. Realizations in accordance with embodiments have been described in the context of particular embodiments. These embodiments are meant to be illustrative and not limiting. Many variations, modifications, additions, and improvements are possible. Accordingly, plural instances may be provided for components described herein as a single instance. Boundaries between various components, operations and data stores are somewhat arbitrary, and particular operations are illustrated in the context of specific illustrative configurations. Other allocations of functionality are envisioned and may fall within the scope of claims that follow. Finally, structures and functionality presented as discrete components in the example configurations may be implemented as a combined structure or component. These and other variations, modifications, additions, and improvements may fall within the scope of embodiments as defined in the claims that follow.

Embodiments in accordance with the disclosure may be implemented in hardware, firmware, software, or any combination thereof. Embodiments may also be implemented as instructions stored using one or more machine-readable media, which may be read and executed by one or more processors. A machine-readable medium may include any mechanism for storing or transmitting information in a form readable by a machine (e.g., a computing device or a "virtual machine" running on one or more computing devices). For example, a machine-readable medium may include any suitable form of volatile or non-volatile memory.

In some embodiments, the master controller 150 is configured to use at least one of artificial intelligence techniques or machine learning techniques to refine parameters of the therapy manufacturing steps as the initial plurality of cells are processed into the final plurality of cells. In some embodiments, in accordance with the present principles, suitable machine learning techniques can be applied to learn commonalities in sequential application programs and for determining from the machine learning techniques at what level sequential application programs can be canonicalized. In some embodiments, machine learning techniques that can be applied to learn commonalities in sequential application programs can include, but are not limited to, regression methods, ensemble methods, or neural networks and deep learning such as 'Se2oSeq' Recurrent Neural Network (RNNs)/Long Short Term Memory (LSTM) networks, graph neural networks applied to the abstract syntax trees corresponding to the sequential program application.

In some embodiments, the machine learning techniques may receive data inputs from sensors and monitoring devices associated with the automated closed apparatus 100, along with user inputs. In some embodiments, the machine learning techniques may receive data inputs as imported data files. For example, data inputs may be derived from 'Omics' technologies such as sequencing or mass spectrometers (offline characterization) which are imported as data files before or during manufacturing of cells using the methods and apparatus described herein. The data collected from one or more of the above sources can be partially, or fully, combined to train the machine learning model.

The artificial intelligence techniques or machine learning techniques may be used to refine parameters of the therapy manufacturing steps as the initial plurality of cells are processed into the final plurality of cells. For example, metabolomics can be performed real time on the plurality of initial cells to provide a detailed fingerprint of the biological function of the cells based on the way they are consuming nutrients and producing metabolic byproducts (Oxygen, $CO_2$, Glucose, pH, ATP, or the like), allowing for a prediction of how much the cells will expand as a function of time, and the machine learning techniques may be used to determine how to adjust the experimental conditions (e.g., add nutrients) to meet certain cell expansion thresholds for the plurality of final cells. In another example, the plurality of initial cells may be characterized by the automated closed apparatus 100 based on a measured size or morphology of the plurality of initial cells, and machine learning techniques may be used to determine subsequent cell manufacturing steps via the one or more auxiliary devices 110 to meet a desired type and quantity of the plurality of final cells.

Figure 3:
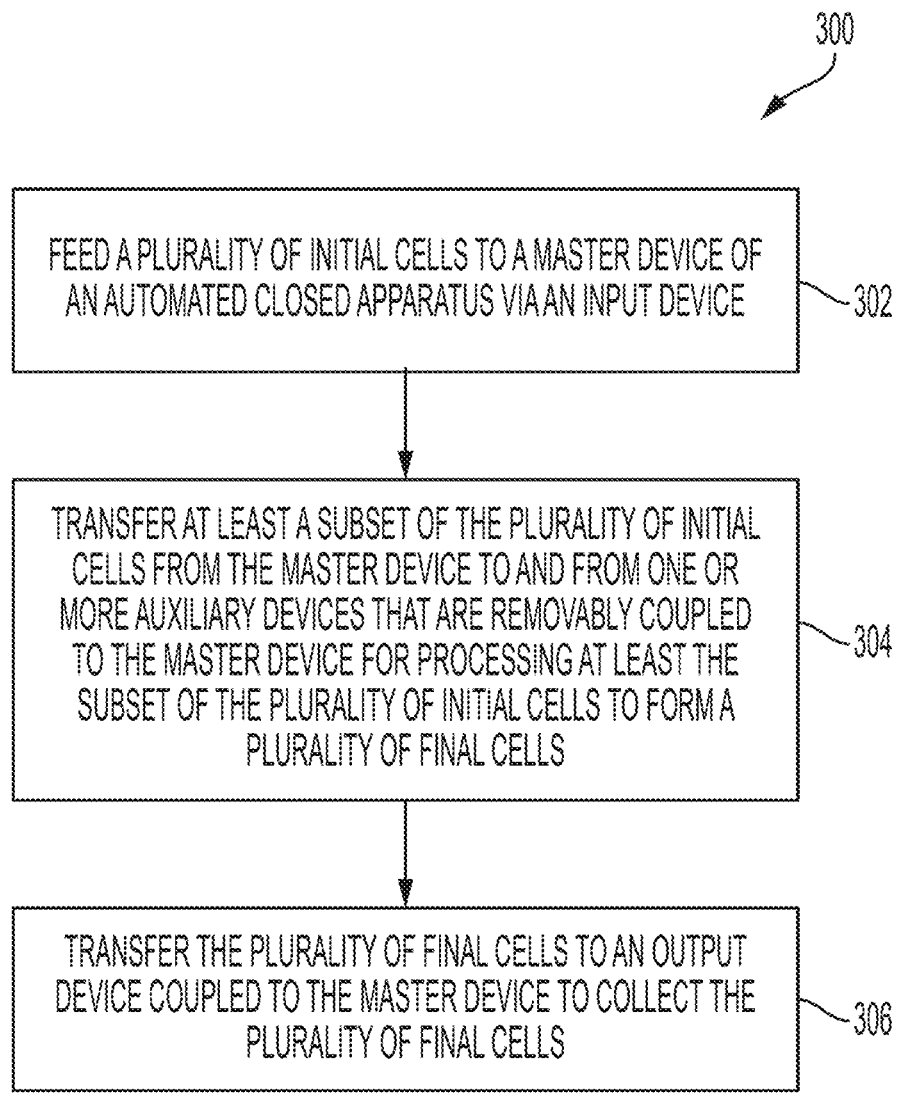
FIG. 3 depicts a flow chart of a method of processing a plurality of cells in an automated closed apparatus in accordance with at least some embodiments of the present disclosure.

FIG. 3 depicts a flow chart of a method 300 of processing a plurality of cells in an automated closed apparatus in accordance with at least some embodiments of the present disclosure. At 302, the method 300 comprises feeding a plurality of initial cells to a master device (e.g., master device 102) of an automated closed apparatus (e.g., automated closed apparatus 100) via an input device (e.g., input device 104). The plurality of initial cells may be T cells, stem cells, or the like. The plurality of initial cells may be in the form of a blood or tissue sample.

At 304, at least a subset of the plurality of initial cells is transferred from the master device to and from one or more auxiliary devices (e.g., one or more auxiliary devices 110) via an input line and an output line of each auxiliary device for processing at least the subset of the plurality of initial cells to form a plurality of final cells. The one or more auxiliary devices are removably coupled to the master device so that the automated closed apparatus may be customized for a variety of cell types and or a variety of cell manufacturing processes. The master device is configured to provide instructions to the one or more auxiliary devices via a master controller (e.g., master controller 150). In some embodiments, the master device is configured to provide instruction for a variety of cell types. In some embodiments, the master controller uses machine learning techniques as described above to provide instructions to the one or more auxiliary devices. The one or more auxiliary devices may perform one or more of any of the processes or function described above.

For example, transferring at least a subset of the plurality of initial cells from the master device to and from the one or more auxiliary devices may comprise at least one of performing a chemical enrichment process on at least the subset of the plurality of initial cells, performing a cleaning process on at least the subset of the plurality of initial cells to remove contamination, modify the cleaned at least subset of the plurality of initial cells via an activation, transduction, or transfection process, and multiplying the modified at least subset of the plurality of initial cells to form the plurality of final cells.

At 306, the plurality of final cells are transferred to an output device (e.g., output device 108) coupled to the master device to collect the plurality of final cells. The output device may perform any fill and finish, final formulation, or cryopreservation steps. In some embodiments, a cell count measurement, or other diagnostic measurement, may be taken of the at least subset of the plurality of initial cells in at least one device of the one or more auxiliary devices, the input device. In some embodiments, a cell count measurement, or other diagnostic measurement, may be taken in the output device.

While the foregoing is directed to embodiments of the present disclosure, other and further embodiments of the disclosure may be devised without departing from the basic scope thereof.

The invention claimed is:

1. An automated closed apparatus for cell therapy manufacturing, comprising:
    a master device having a master controller for processing control programs for a variety of cells, wherein the master device includes a reservoir and a flow control switch fluidly coupled to the reservoir, wherein the flow control switch includes a plurality of ports configured to selectively direct fluids between the master device and one or more auxiliary devices that may be coupled to the plurality of ports;
    an input device fluidly coupled to the master device, wherein the input device is configured to feed an initial plurality of cells to the reservoir of the master device;
    wherein the one or more auxiliary devices are disposed external to the master device, wherein each of the one or more auxiliary devices is configured to perform one or more cell therapy manufacturing steps to the initial plurality of cells to form a final plurality of cells, wherein each of the one or more auxiliary devices is removably coupled to the master device via any of the plurality of ports of the flow control switch, wherein, when coupled to the master device, each device of the one or more auxiliary devices is (1) fluidly coupled to the master device via one or more transfer lines to facilitate transfer of at least a portion of the initial plurality of cells therebetween; and (2) electrically coupled to the master device to facilitate transfer of data therebetween, wherein the master device facilitates one or more cell therapy manufacturing steps via the one or more auxiliary devices; and
    an output device coupled to the master device configured to collect the final plurality of cells from the master device.

2. The automated closed apparatus of claim 1, wherein each of the one or more auxiliary devices includes a controller configured to communicate with the master controller of the master device.

3. The automated closed apparatus of claim 1, wherein the master controller is configured to use at least one of artificial intelligence techniques or machine learning techniques to refine parameters of the one or more cell therapy manufacturing steps as the initial plurality of cells are processed into the final plurality of cells.

4. The automated closed apparatus of claim 1, wherein one of the one or more auxiliary devices is configured to perform a chemical enrichment process or a cleaning process on the at least a portion of the plurality of initial cells.

5. The automated closed apparatus of claim 1, further comprising a flow valve disposed between the reservoir and the flow control switch and a pressure system coupled to the flow valve.

6. The automated closed apparatus of claim 1, wherein one of the one or more auxiliary devices performs a cell selection process to select a subset of the plurality of initial cells for gene modification.

7. The automated closed apparatus of claim 1, wherein one of the one or more auxiliary devices performs an activation, transduction, or transfection process on a subset of the plurality of initial cells.

8. The automated closed apparatus of claim 1, wherein the one or more auxiliary devices includes a bioreactor for multiplying a subset of the plurality of initial cells to form the plurality of final cells.

9. The automated closed apparatus of claim 1, wherein the one or more auxiliary devices comprise auxiliary devices configured to perform the following processes on the at least a portion of the plurality of initial cells, wherein each process is performed in a different auxiliary device:
    an analysis or diagnosis process;
    a chemical enrichment process;
    a cleaning process to remove contamination;
    a cell selection process;
    an activation, transduction, or transfection process;
    a perfusion process;
    a cell expansion process to form the plurality of final cells; and a fill and finish process.

10. The automated closed apparatus of claim 1, wherein the reservoir includes one or more ports for in-line monitoring devices and sensors.

11. A method for processing a plurality of cells in an automated closed apparatus, comprising:
    feeding a plurality of initial cells to the master device of the automated closed apparatus of claim 1 via the input device;
    transferring at least a subset of the plurality of initial cells from the master device to and from the one or more auxiliary devices for processing at least the subset of the plurality of initial cells to form a plurality of final cells; and
    transferring the plurality of final cells to the output device coupled to the master device to collect the plurality of final cells.

12. The method of claim 11, wherein transferring at least a subset of the plurality of initial cells from the master device to and from the one or more auxiliary devices comprises:
    performing a chemical enrichment process on at least the subset of the plurality of initial cells;
    performing a cleaning process on at least the subset of the plurality of initial cells to remove contamination;

modifying the cleaned at least subset of the plurality of initial cells via an activation, transduction, or transfection process; and multiplying the modified at least subset of the plurality of initial cells to form the plurality of final cells.

13. The method of claim 11, wherein the plurality of initial cells are T cells or stem cells.

14. The method of claim 11, further comprising taking a cell count of the at least a subset of the plurality of initial cells in at least one device of the one or more auxiliary devices.

15. The method of claim 11, wherein the master device uses at least one of artificial intelligence techniques or machine learning techniques to provide instructions to the one or more auxiliary devices.

16. A non-transitory computer readable medium for storing computer instructions that, when executed by at least one processor causes the at least one processor to perform the method of claim 11.

17. The non-transitory computer readable medium of claim 16, wherein transferring at least a subset of the plurality of initial cells from the master device to and from the one or more auxiliary devices comprises:

performing a chemical enrichment process on at least the subset of the plurality of initial cells;

performing a cleaning process on at least the subset of the plurality of initial cells to remove contamination;

modifying the cleaned at least subset of the plurality of initial cells via an activation, transduction, or transfection process; and multiplying the modified at least subset of the plurality of initial cells to form the plurality of final cells.

18. The non-transitory computer readable medium of claim 16, wherein the plurality of initial cells are T cells or stem cells.

19. The non-transitory computer readable medium of claim 16, further comprising taking a cell count of the at least a subset of the plurality of initial cells in at least one device of the one or more auxiliary devices.

20. The non-transitory computer readable medium of claim 16, wherein the master device uses at least one of artificial intelligence techniques or machine learning techniques to provide instructions to the one or more auxiliary devices.

* * * * *